(12) United States Patent
Melis et al.

(10) Patent No.: US 6,989,252 B2
(45) Date of Patent: Jan. 24, 2006

(54) HYDROGEN PRODUCTION USING HYDROGENASE-CONTAINING OXYGENIC PHOTOSYNTHETIC ORGANISMS

(75) Inventors: Anastasios Melis, El Cerrito, CA (US); Liping Zhang, Kensington, CA (US); John R. Benemann, Walnut Creek, CA (US); Marc Forestier, Lakewood, CO (US); Maria Ghirardi, Lakewood, CO (US); Michael Seibert, Lakewood, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 09/748,690

(22) Filed: Dec. 22, 2000

(65) Prior Publication Data

US 2001/0053543 A1  Dec. 20, 2001

Related U.S. Application Data

(60) Provisional application No. 60/173,391, filed on Dec. 28, 1999.

(51) Int. Cl.
*C12P 3/00* (2006.01)
*C12N 1/12* (2006.01)

(52) U.S. Cl. .................. 435/168; 435/257.1; 435/257.6; 435/946

(58) Field of Classification Search ................ 435/168, 435/257.1, 257.6, 946
See application file for complete search history.

(56) References Cited

U.S. PATENT DOCUMENTS

| 4,442,211 A | 4/1984 | Greenbaum ................. 435/168 |
| 4,532,210 A | 7/1985 | Miura et al. ................ 435/168 |

OTHER PUBLICATIONS

Melis, A. et al., "Sustained Photobiological Hydrogen Gas Production Upon Reversible Inactivation of Oxygen Evolution in Green Alga *Chlamydomonas reinhardtii*," Proceedings of the 1999 U.S. DOE Hydrogen Program Review, NREL/CP–570–26938.

Benemann, J.R., "Hydrogen Biotechnology Progress and Prospects," Nature Biotechnol. 14: 1101–1103 (1996).

*Primary Examiner*—Vera Afremova
(74) *Attorney, Agent, or Firm*—Paul J. White

(57) ABSTRACT

A reversible physiological process provides for the temporal separation of oxygen evolution and hydrogen production in a microorganism, which includes the steps of growing a culture of the microorganism in medium under illuminated conditions to accumulate an endogenous substrate, depleting from the medium a nutrient selected from the group consisting of sulfur, iron, and/or manganese, sealing the culture from atmospheric oxygen, incubating the culture in light whereby a rate of light-induced oxygen production is equal to or less than a rate of respiration, and collecting an evolved gas. The process is particularly useful to accomplish a sustained photobiological hydrogen gas production in cultures of microorganisms, such as *Chlamydomonas reinhardtii*.

8 Claims, 5 Drawing Sheets

HYDROGEN PRODUCTION USING HYDROGENASE-CONTAINING OXYGENIC PHOTOSYNTHETIC ORGANISMS

CROSS REFERENCE TO RELATED APPLICATIONS

Pursuant to 35 U.S.C 119(e), this application is a 35 USC 111(a) application claiming the benefit of the 35 USC 111(b) application, U.S. Ser. No. 60/173,391, filed Dec. 28, 1999.

CONTRACTUAL ORIGIN OF THE INVENTION

The United States Government has rights in this invention pursuant to Contract No. DE-AC36-99-GO10337 between the United States Department of Energy and the Midwest Research Institute and pursuant to Contract No. DE-FC36-98 G0010278 between the United States Department of Energy and the University of California at Berkley.

BACKGROUND OF THE INVENTION

1. Field of the Invention

This invention relates to photosynthetic hydrogen production and specifically to a biophotolysis process, which can be cycled, for the temporal separation of oxygen evolution and hydrogen production in algae.

2. Description of the Related Art

New clean energy sources that are free of environmental pollution have been sought worldwide as a substitute for fossil fuels. Among the potential sources, the photobiological production of hydrogen by procaryotic or eucaryotic organisms is a desirable way of generating a renewable hydrogen fuel from light and water, which are among nature's most plentiful resources.

The ability of green algae, such as *Chlamydomonas reinhardtii*, to produce hydrogen from water has been recognized for over 55 years. This reaction is catalyzed by the reversible hydrogenase, an enzyme that is induced in the cells after exposure to a short period of anaerobiosis. However, the activity is rapidly lost, as soon as the light is turned on, because of immediate inactivation of the reversible hydrogenase by photosynthetically generated $O_2$.

In the prior art, certain methods have been used to circumvent the inactivation problem. U.S. Pat. No. 4,532,210 discloses the biological production of hydrogen in a algal culture using an alternating light and dark cycle. The process comprises alternating a step for cultivating the alga in water under aerobic conditions in the presence of light to accumulate photosynthetic products (starch) in the alga and a step for cultivating the alga in water under microaerobic conditions in the dark to decompose the material accumulated by photosynthesis to evolve hydrogen. This method uses a nitrogen gas purge technique to remove oxygen, carried over from the light cycle, from the culture.

U.S. Pat. No. 4,442,211 discloses that the efficiency of a process for producing hydrogen, by subjecting algae in an aqueous phase to light irradiation, is increased by culturing algae which has been bleached during a first period of irradiation in a culture medium in an aerobic atmosphere until it has regained color and then subjecting these algae to a second period of irradiation wherein hydrogen is produced at an enhanced rate. A reaction cell is used in light irradiating the culture in an environment that is substantially free of $CO_2$ and atmospheric $O_2$. This environment is maintained by passing an inert gas (e.g. helium) through the cell to remove all hydrogen and oxygen generated by the splitting of water molecules in the aqueous medium. Although continuous purging of $H_2$-producing cultures with inert gases has allowed for the sustained production of $H_2$, such purging is expensive and impractical for large-scale mass cultures of algae.

The use of exogenous reductants, such as sodium dithionite, as well as the addition of herbicides to inhibit photosynthetic $O_2$ evolution, has also been used, but these methods are either impractical or create an irreversible condition that may lead to cell death.

An alternative approach to photoproduce hydrogen is based on the concept of indirect biophotolysis in which metabolite accumulation by photosynthesis serves as a substrate for subsequent hydrogen production. In this approach, the two reactions, photosynthesis and $H_2$ production, are spatially and/or temporally, separated from each other. See e.g., Benemann, J. R. Hydrogen Biotechnology: Progress and Prospects. *Nature Biotechnol.* 14: 1101–1103 (1996).

In view of the foregoing a need exists for a sustainable process of photosynthetic hydrogen production in an algal culture. Unlike the foregoing methods, which rely on a mechanical means or chemical manipulations to the cells, the sustainable process would desirably overcome the hydrogenase oxygen-sensitivity problem through a low cost physiological response.

BRIEF SUMMARY OF THE INVENTION

Therefore, it is an object of the invention to provide a physiological and reversible process for the temporal separation of oxygen evolution and hydrogen production in an algal culture in order to avoid the deactivation of hydrogenase in the presence of oxygen.

It is a further object of the invention to provide a process of sustained photobiological hydrogen gas production in a *Chlamydomonas reinhardtii* culture.

Briefly, the invention provides a reversible physiological process for the temporal separation of oxygen evolution and hydrogen production in a microorganism, which includes the steps of growing a culture of the microorganism in medium under illuminated conditions to accumulate an endogenous substrate, depleting from the medium a nutrient selected from the group consisting of sulfur, iron, and/or manganese, sealing the culture from atmospheric oxygen, incubating the culture in light whereby a rate of light-induced oxygen production is equal to or less than a rate of respiration, and collecting an evolved gas.

BRIEF DESCRIPTION OF THE SEVERAL VIEWS OF THE DRAWINGS

The present invention is illustrated by way of example and not limitation in the accompanying figures in which like reference numerals indicate similar elements and in which.

DETAILED DESCRIPTION OF THE DRAWINGS

Figure 1:
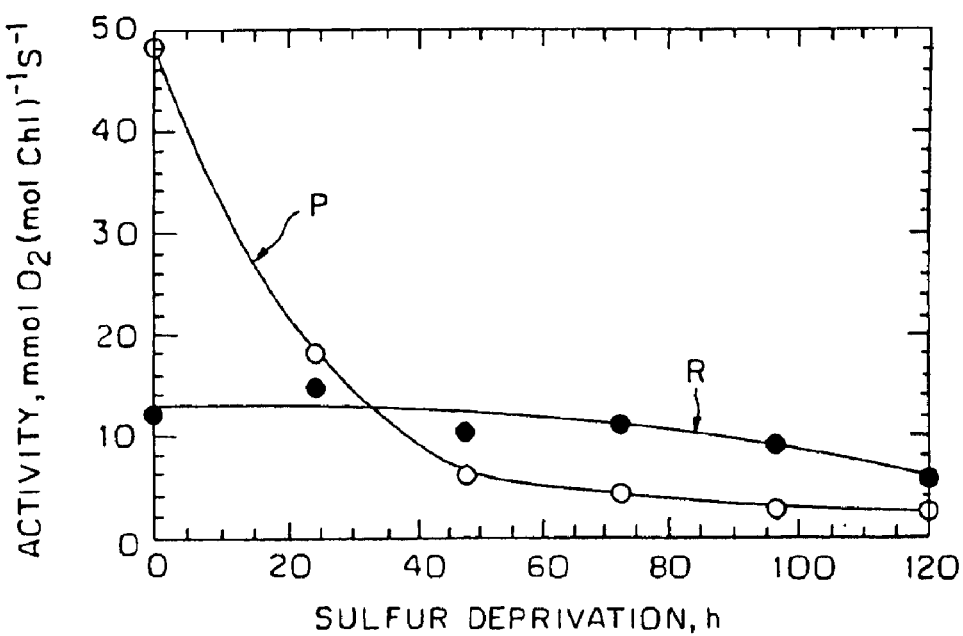
FIG. 1 is the absolute activity of oxygenic photosynthesis (P) and oxidative respiration (R) in *C. reinhardtii* cells suspended in a medium devoid of sulfur. Incubation under sulfur deprived conditions started at 0 h. Cells were suspended in the presence of 10 mM $NaHCO_3$, pH 7.6. The rate of cellular respiration (R) was recorded in the dark from aliquots of cells taken from a culture at the indicated times, followed by a measurement of the rate of light-saturated photosynthesis (P). Rates of photosynthesis were corrected for the rate of dark respiration.

Unless specifically defined otherwise, all technical or scientific terms used herein have the same meaning as commonly understood by one of ordinary skill in the art to which this invention belongs. The phrase "oxygen evolution" refers to photosynthetically produced oxygen which is not metabolized by respiration and comes out of the cell. Although any methods and materials similar or equivalent to those described herein can be used in the practice or testing of the present invention, the preferred methods and materials are now described.

The invention provides a process for sustained photobiological production of $H_2$ gas via the reversible hydrogenase pathway in the green alga *Chlamydomonas reinhardtii*. This single-organism, two-stage $H_2$ production method, that can be repeated in cycles, circumvents the severe $O_2$-sensitivity of the reversible hydrogenase by temporally separating photosynthetic $O_2$ evolution and carbon accumulation (Stage 1) from consumption of cellular metabolites, reduced levels of water-oxidation, and concomitant $H_2$ production (Stage 2). A transition from Stage 1 to Stage 2 was effected upon sulfur deprivation of the culture, which reversibly inactivated much of the photosystem-II activity and $O_2$ evolution. Acetate may be required for this process. Under these conditions, oxidative respiration by the cells in the light, depleted $O_2$ and caused anaerobiosis in the culture, which was necessary and sufficient for the induction of the reversible hydrogenase. Subsequently, sustained cellular $H_2$ gas production was observed in the light, but not in the dark. The mechanism of $H_2$ production entailed utilization of electrons from both residual water-oxidation activity of photosystem II (the source of most reductant for $H_2$ production) and also from endogenous substrate catabolism which is coupled to the consumption of $O_2$ generated by the residual water-oxidation activity during hydrogen production. Protein catabolism and electron transport from endogenous substrate to the cytochrome $b_6$-f and photosystem-I complexes in the chloroplast thylakoids may also occur. Light absorption by photosystem-I was required for $H_2$ production, suggesting that photoreduction of ferredoxin is followed by electron donation to the reversible hydrogenase. The latter catalyzes the reduction of protons to molecular $H_2$ in the chloroplast stroma.

EXAMPLE 1

Growth of the Algae

*Chlamydomonas reinhardtii* strain C137 (mt$^+$) was grown photoheterotrophically in a Tris-acetate-phosphate (TAP) medium, pH 7. Liquid cultures, bubbled with 3% $CO_2$ in air, were grown at 25° C. in flat bottles (3–5 cm optical path length) upon stirring and under continuous cool-white fluorescence illumination at ~200 $\mu$mol of photons m$^{-2}$ s$^{-1}$. Culture density was measured by cell counting with the improved Neubauer ultraplane hemacytometer and an Olympus BH-2 light microscope operated at a magnification of 200x. Cells were grown to the late logarithmic phase (about 3–6$\times 10^6$ cells/ml). After they reached this density, cells were suspended in the absence of sulfur and incubated under continuous illumination for up to 150 h in the same light but without $CO_2$ bubbling. The sulfur-free medium was also but not limited to a Tris-acetate-phosphate medium in which $MgCl_2$, $ZnCl_2$, $CuCl_3$ and $FeCl_3$ are used instead of the respective sulfates. The cells could be cultured at up to saturating light intensity and at any temperature at which they can survive.

Oxygen Exchange and Hydrogen Evolution Measurements

Exchange activity of the cultures was measured at 25° C. with a Clark-type $O_2$ electrode illuminated with a slide projector lamp. Yellow actinic excitation of saturating intensity was provided by a CS 3-69 Corning cut-off filter. A 5 ml aliquot of the culture was supplemented with 100 $\mu$L of 0.5 M $NaHCO_3$, pH 7.4. Measurements were taken with the $O_2$ electrode, beginning with the registration of dark respiration in the cell suspension, and followed by measurement of the light-saturated rate of $O_2$ evolution. The rate of each process was recorded for about 5 minutes. Evolution activity of $O_2$ and $H_2$ was measured with two different Clark-type electrodes, each poised for the optimal measurement of $O_2$ and $H_2$, respectively. Saturating actinic illumination of about 1,300 $\mu$mol photons m$^{-2}$ s$^{-1}$ was provided by a Nolan-Jenner Model 170-D high intensity actinic source, filtered through a 1% $CuSO_4$ solution. Samples for $H_2$ evolution measurements were transferred from the culture bottle with argon-flushed gas-tight syringes into the argon-flushed Clark-type electrode chamber. The chamber was then bubbled with argon for ~3 min to remove $H_2$ dissolved into the growth medium. The $H_2$ concentration signal from the electrode was amplified with an in-line Ithaco Model 1201 amplifier, modified with a custom-built current-to-voltage converter and analyzed with a Data Translation DT31-EZ A/D data acquisition system using customized DTVee software. Photosynthetic $O_2$ evolution and oxidative respiration rates were measured as described above.

Gas Collection Measurements

Culture bottles (Schott or Roux type) were fitted with an #25 Ace thread and smaller side-ports for liquid sampling. A threaded glass stopper with capillaries for gas sampling was fitted with a Viton O-ring and used to seal the reactor.

Threaded side-arm and gas sampling ports were sealed with rubber laminated Teflon septa. Teflon tubing (Aminco, HPLC), attached to one of the gas ports, was used to conduct gas evolved by the algae in the culture bottles to an upside-down graduated cylinder filled with $H_2O$. The gas collection tubing was detached from the culture bottle during liquid and gas sampling to avoid disturbance of gas volume readings in the graduated cylinder.

Determination of the Concentrations of $CO_2$ and $H_2$

A Varian Model 3760 gas chromatograph with Varian Star 4.0 data analysis software was used to determine the levels of $CO_2$ and $H_2$ in the headspace of the reactor. A Supelco MS-5A molecular sieve column with argon as the carrier gas was used to separate $O_2$, $N_2$, and $H_2$. A Supelco Porapak Q column with He as the carrier gas was used to assay for $CO_2$. Signals were generated by the instrument's TC detector. Dissolved $CO_2$ was driven into the gas phase by injection of the liquid sample into 2N hydrochloric acid in an argon-flushed, septum-capped vial. The signals were calibrated by injection of known amounts of $O_2$, $N_2$, $H_2$, and $CO_2$.

Thylakoid Membrane Isolation and Analysis

Cells were harvested by centrifugation at 3,000×g for 3 min at 4° C. Pellets were diluted with sonication buffer containing 100 mM Tris-HCl (pH 6.8), 10 mM NaCl, 1 mMp-aminobenzamidine-2HCI, 1 mM 6-aminocaproic acid, 10 mM EDTA, and 100 PM PMSF. Cells were disrupted by sonication for 2 min in a Branson Sonifier (cell Disruptor 200) operated in the pulsed mode with a 50% duty cycle and an output power setting of 5. Unbroken cells and other large cell fragments were removed by centrifugation at 3,000×g for 3 min at 4° C. The supernatant was then centrifuged at 75,000×g for 30 min at 4° C. Chlorophyll (a+b) content of the samples was measured in 80% acetone by the method of Arnon (1949).

Spectrophotometric Measurements

The amplitude of the light minus dark absorbance difference measurements at 700 and 320 nm was employed for the direct quantitation of P700 and $Q_A$ in the *C. reinhardtii* cultures (Melis, 1989; 1991). These measurements provided estimates of the concentration of functional PSI and PSII reaction centers, respectively in the samples at various times following sulfur deprivation. The amplitude of the hydroquinone-reduced minus ferricyanide-oxidized absorbance difference measurement at 554 nm, with isosbestic points at 544 and 560 nm, was employed in the quantitation of cytochromef Thylakoid membrane purification and preparation for these measurements were described earlier (Melis et al., 1996).

Quantitative Analysis of Acetate, Starch, and Protein

The level of acetate was measured in the supernatant of the culture, following centrifugation of the algal cells at 1,000×g for 2 min. A Hewlett-Packard 1050 fully integrated HPLC with a BioRad Aminex HPX-87H ion exchange column and UV detector was used for these measurements. $H_2SO_4$ (4 mM) served as the mobile phase to separate organic acids. The output signals were analyzed with HP Chemstation software. Starch determinations were performed using amyloglucosidase (Sigma, St. Louis) to convert starch from methanol-solubilized cells to glucose. The concentration of glucose was then determined using a D-Glucose test kit (Boehringer Mannheim). The test depends upon two enzymatic reactions, the phosphorylation of glucose to glucose 6-phosphate by hexokinase, and subsequent reduction of $NAD^+$ to NADH by glucose 6-phosphate. The amount of NADH accumulated was measured spectrophotometrically by determining the absorption change at 340 nm. Protein quantitation was implemented according to the Lowry method.

Sustained Photobiological Production of Hydrogen Gas in *C. reinhardtii*

When *Chlamydomonas reinhardtii* cultures are deprived of inorganic sulfur (<100 $\mu$M), the light-saturated rates of $O_2$ evolution and $CO_2$ fixation decline significantly within 24 h in the light, without a proportional loss of chloroplast or thylakoid membrane electron transport components. Analysis indicated that such loss in electron transport activity is due to the conversion of PSII centers from the $Q_B$-reducing to $Q_{B'}$-nonreducing form. The results of inorganic sulfur deprivation on photosynthesis and cellular respiration over a longer period of time (0–120 h) are shown in FIG. 1. The activity of photosynthesis, measured from the light-saturated rate of $O_2$ evolution in *Chiamydomonas reinhardtii* (FIG. 1, P), declined biexponentially from 48 mmol $O_2$ (mol Chl)$^{-1}$ s$^{-1}$ at t=0 h to less than 3 mmol $O_2$ (mol Chl)$^{-1}$ S$^{-1}$ at t=120 h. Cellular respiration, measured from the rate of $O_2$ consumption in the dark (FIG. 1, R), remained fairly constant at about 13 mmol $O_2$ (mol Chl)$^{-1}$ s$^{-1}$ over the 0–70 h period and declined slightly thereafter. The absolute activity of photosynthesis decreased below the level of respiration in *Chlamydomonas reinhardtii* after about 24–30 h of sulfur deprivation. Slower inactivation results were obtained with iron (<1.0 $\mu$M) or manganese (<1.0 $\mu$M) deprivation.

After about 24–30 h of sulfur deprivation, a sealed *Chlamydomonas reinhardtii* culture quickly became anaerobic in the light due to the greater rate of respiration than photosynthesis of the cells. This was confirmed by measurements with a Clark-type $O_2$ electrode (results not shown). It was of particular interest, therefore, to test whether the hydrogenase activity of the cells could be induced and sustained under these conditions. As shown below, anaerobiosis (but not darkness) is necessary and sufficient for induction of the reversible hydrogenase and for light-induced $H_2$-production activity in *C. reinhardii*.

EXAMPLE 2

Figure 2A:
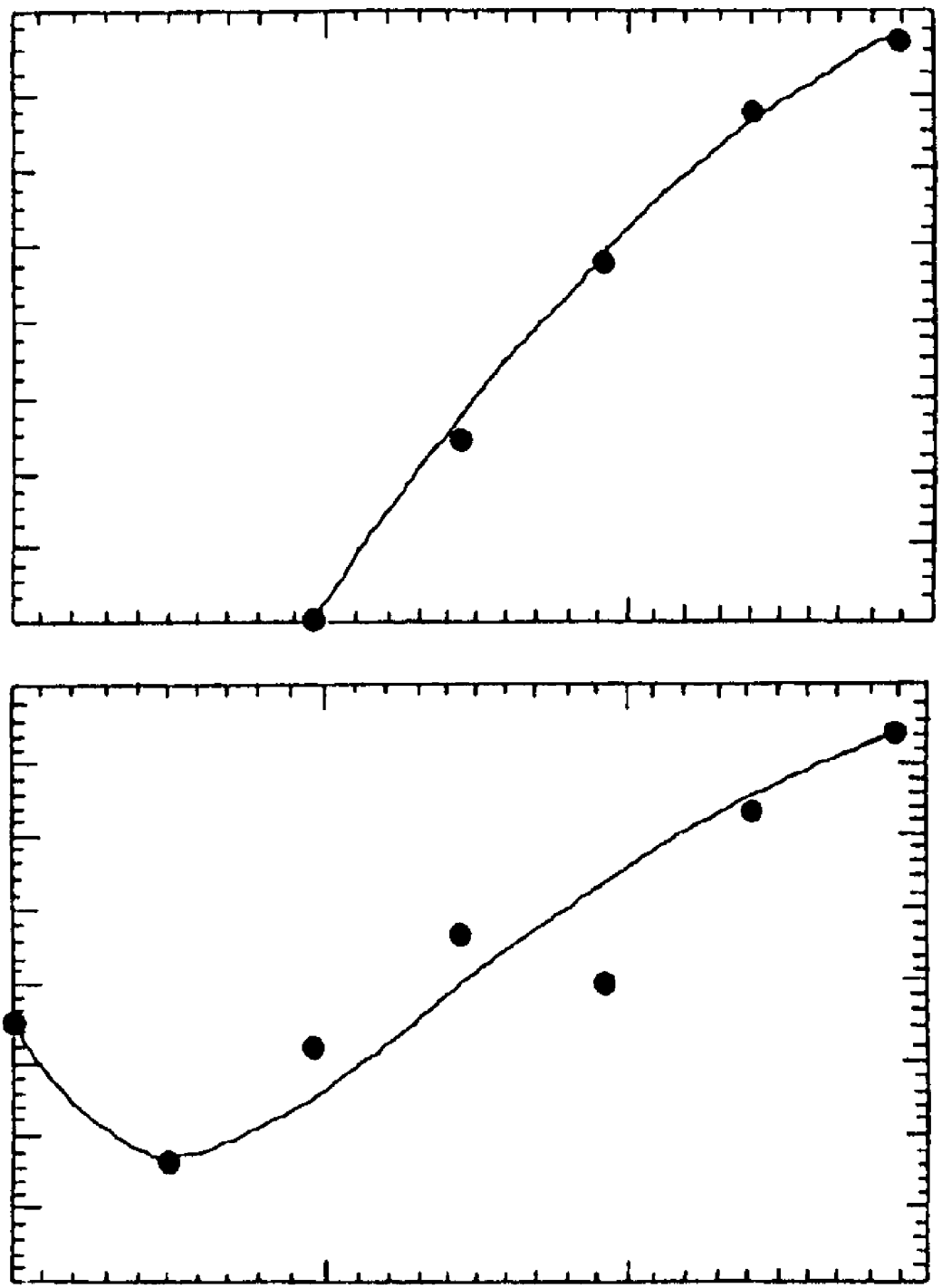
FIG. 2. (A) Hydrogen gas volume accumulated by displacement of water in an inverted graduated cylinder as a function of cell incubation time in the absence of sulfur. (B) Quantitation of dissolved $CO_2$ produced in tandem with $H_2$ by sulfur-deprived *C. reinhardtii*. The culture was sealed at about 45 h after suspension of the cells in a sulfur-free medium. Values correspond to 1 L culture.

FIG. 2 shows the result of such measurements with a sulfur-deprived culture of *C. reinhardtii*. In this experiment, a 1-L culture of algae at a cell density of about 6×10$^6$ cells/ml was incubated in sulfur-deprived medium under continuous illumination. The sulfur-depleted medium was also but not limited to Tris-acetate-phosphate medium in which $MgCl_2$, $ZnCl_2$, $CuCl_2$, and $FeCl_3$ are used instead of the respective sulfates. The cells could be cultured at up to saturating light intensity and at any temperature at which they can survive. The flask was sealed 24 h after S-deprivation, when the rate of photosynthetic $O_2$ evolution was determined to be equal to or less than the rate of respiration. Hydrogen evolution activity, measured with a Clark-type $H_2$ electrode (Seibert et al., 1998), was detected in aliquots taken from the culture at t>35 h (results not shown). Thus, sulfur deprivation itself does not appear to exert a negative effect on the induction of the reversible hydrogenase. Hydrogen gas accumulation was determined by measuring the amount of water that was displaced in an inverted graduated cylinder (FIG. 2A). The rate of gas accumulation was constant at about 2 ml h$^{-1}$ (equivalent to 1.2 mmol H$_2$ [mol Chl]$^{-1}$ s$^{-1}$) for up to about 120 h and slightly declined thereafter. Gas chromatographic analysis revealed that the composition of gasses in the headspace of the culture bottle at 150 h was about 87% H$_2$, 1% CO$_2$, with the remainder being N$_2$ and traces of O$_2$.

Figure 2B:
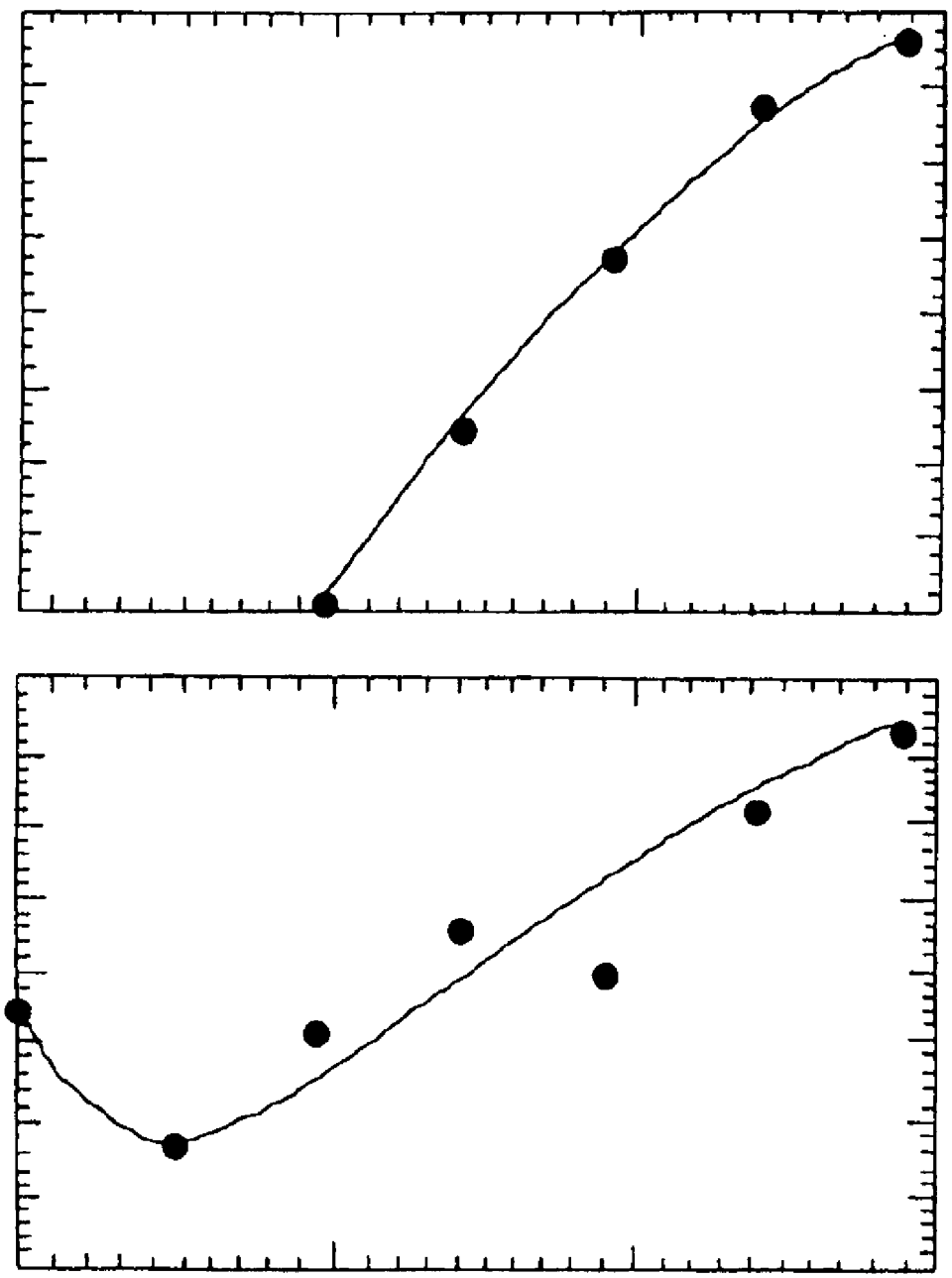

In addition to H$_2$, algal anaerobic photofermentations should produce CO$_2$ and small amounts of formate and ethanol. FIG. 2B shows that the amount of dissolved CO$_2$ (about 1.8 mmol per L) declined during the 0–30 h period and subsequently increased during the 50–150 h period from about 1.25 to about 3.7 mmol CO$_2$ per L culture. From the results of FIG. 2A and FIG. 2B, we estimated a H$_2$/CO$_2$ (mol:mol) ratio of about 2:1 for this process (see also Table I). The amount of gaseous CO$_2$ in the headspace of the culture increased gradually from atmospheric values (0.03%) to about 1% during the course of the H$_2$-production period. This corresponds to a rate of CO$_2$ accumulation less than 0.5% of the rate of H$_2$ accumulation (v:v), and it is negligible compared to the amount of CO$_2$ that accumulated in the liquid phase. Furthermore, accumulation of fermentation byproducts, such as formate and ethanol, was detected.

EXAMPLE 3

Figure 3:
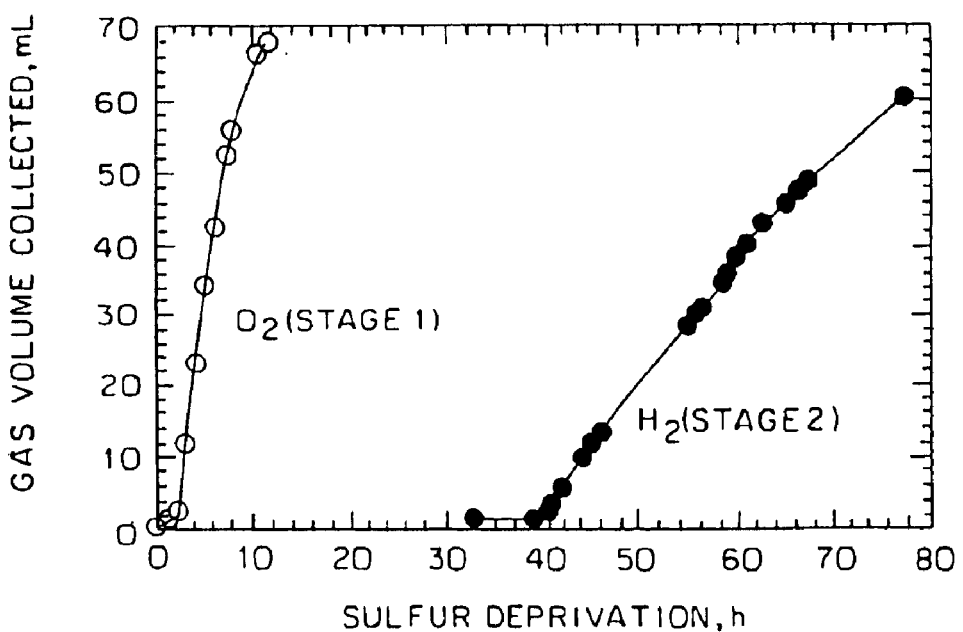
FIG. 3. Stage 1→Stage 2 temporal separation of photosynthetic $O_2$ evolution and $H_2$ gas production by *C. reinhardtii* cells suspended in a sulfur-free medium. Gases were collected in inverted graduated cylinders by the displacement of water.

FIG. 3 shows the result of experiments in which sulfur-deprived cultures were supplemented with 25 mM NaHCO$_3$, pH 7.6, to serve as the substrate of oxygenic photosynthesis. C. reinhardtii cultures grown in a Roux bottle (850 ml capacity), and having a density of about 3x10$^6$ cells/ml, were incubated in the sulfur-deprived medium in the light. The sulfur-free medium was also but not limited to tris-acetate-phosphate medium in which MgCl$_2$, ZnCl$_2$, CuCl$_2$ and FeCl$_3$ are used instead of the respective sulfates. The cells could be cultured at up to saturating light intensity and at any temperature at which they can survive. Cultures were sealed at 0 h and O$_2$ gas collection was measured with the inverted graduated cylinder setup (Stage 1). In Stage 1, the rate of O$_2$ gas accumulation (estimated from the slope of the line in FIG. 3, O$_2$) was about 12 ml O$_2$ h$^{-1}$ (equivalent to 25 $\mu$mol O$_2$ (mol Chl)$^{-1}$ s$^{-1}$) This rate, not corrected for cellular respiration, is comparable to the average of the rates measured with a Clark-type O$_2$ electrode between 0 and 10 h of sulfur deprivation (FIG. 1P). Hydrogen gas accumulation was measured with the same setup at later times, following the onset of anaerobiosis in the sealed cultures (Stage 2). The rate of hydrogen gas accumulation (FIG. 3, H$_2$) was estimated to be about 2 ml H$_2$ h-1 (equivalent to 4.1 mmol H$_2$ (mol Chl)$^{-1}$ s$^{-1}$), which is less than 20% of the rate of O$_2$ gas collected in the inverted graduated cylinder (FIG. 3, O$_2$). The above results show a H$_2$:O$_2$=0.17:1 (mol:mol) ratio. If the entire electron-transport capacity of the photosynthetic apparatus were directed toward H$_2$ production during Stage 2, then one would expect a theoretically maximum H$_2$:O$_2$ (mol:mol) ratio of 2:1. Note that the process described in FIG. 3 can be repeated if depleted cells are regenerated under aerobic photosynthetic conditions in the presence of sulfur prior to re-exposure to sulfur-deprived conditions.

EXAMPLE 4

Figure 4:
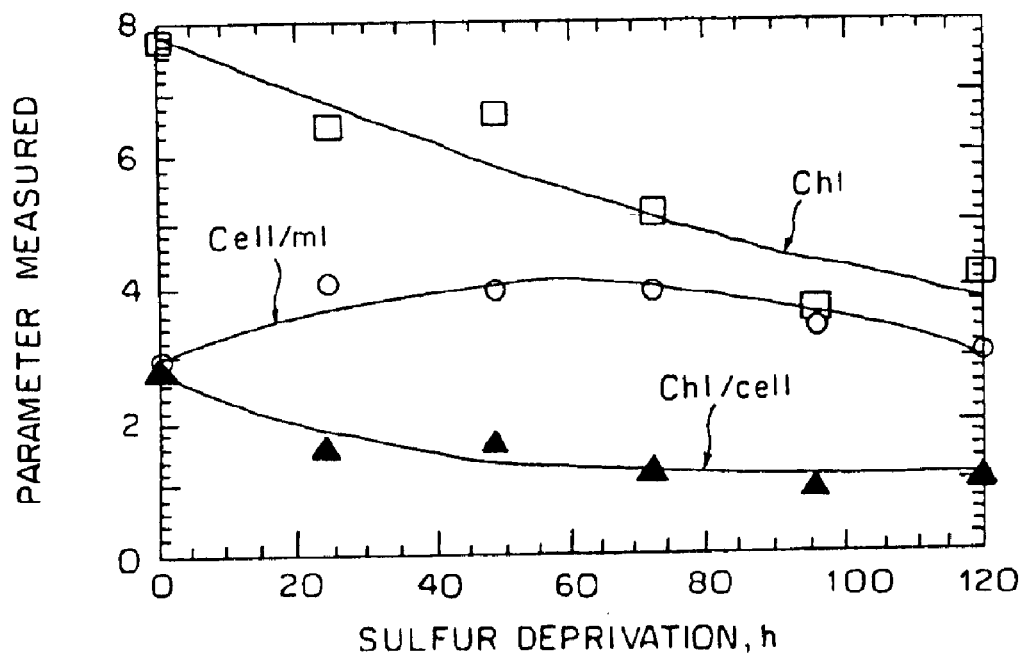
FIG. 4. Chlorophyll concentration, cell density and chlorophyll content per cell in a sulfur-deprived *C. reinhardtii* culture. Initial values, at t=0 h, were Chl=7.7 $\mu$M, Cell/ml= $2.8 \times 10^6$, Chl/cell=$2.8 \times 10^{-15}$ mol/cell.

Structural and Functional Properties of the Hydrogen-Producing Photosynthetic Apparatus The Chl content of the cells and the composition of the thylakoid membrane in C. reinhardtii change upon sulfur deprivation. FIG. 4 shows that the cell density of the culture increased transiently from about 3x10$^6$ cells/ml at 0 h to about 4x10$^6$ cells/ml at 60 h, and subsequently declined to 3x10$^6$ cells/ml at 120 h of sulfur deprivation. Concomitantly, the Chl content of the culture declined steadily from about 8 $\mu$M to about 4 $\mu$M over the duration of this experiment. The Chl content per cell declined from about 2.8x10$^{-15}$ mol Chl/cell to about 1x10$^{-15}$ mol Chl/cell after 120 h of sulfur deprivation. These results show that some cell division does occur during the first 60 h of sulfur deprivation but that a gradual loss of Chl also occurs throughout the deprivation period. The Chl a/Chl b ratio of the cells increased only slightly (by about 10–20%) in the 0–120 h sulfur deprivation period.

Figure 5:
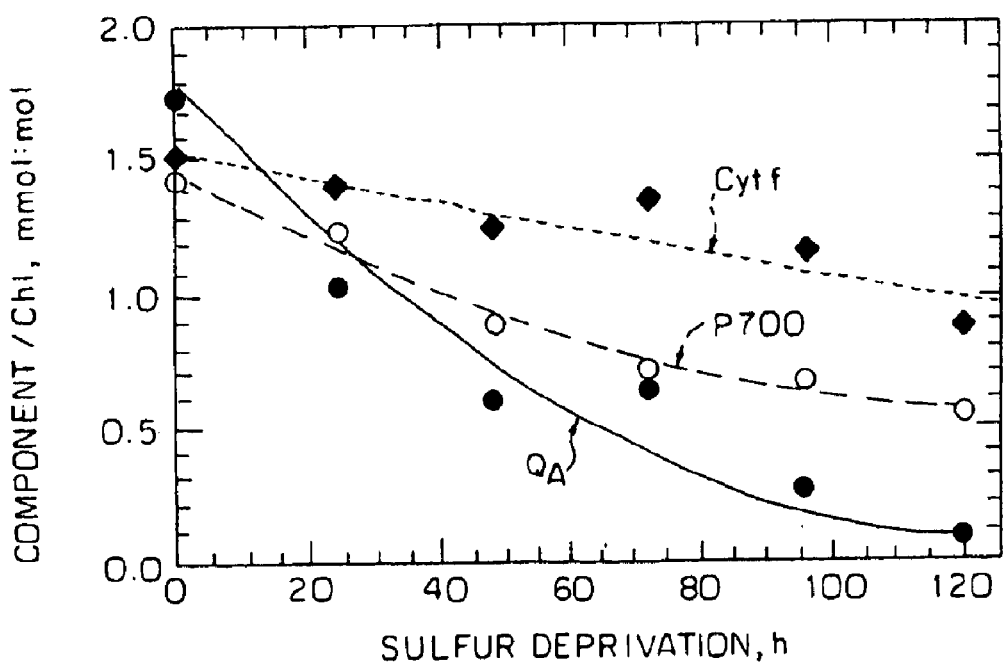
FIG. 5. Concentration of functional PSII ($Q_A$), cytochrome $b_6$-f complex (Cyt f) and PSI (P700) as a function of time in sulfur-deprived *C. reinhardtii*.

The concentration of functional integral thylakoid membrane complexes (PSII, Cyt b$_6$-f and PSI) in the thylakoid membrane of sulfur-deprived C. reinhardtii was investigated spectrophotometrically as follows: (a) from the amplitude of the light-minus-dark absorbance change at 320 nm (measuring the photochemical reduction of the primary quinone acceptor Q$_A$, of PSII); (b) from the amplitude of the light-minus-dark absorbance change at 700 nm (measuring the photochemical oxidation of the reaction center P700 of PSI); and (c) from the hydroquinone-reduced minus ferricyanide-oxidized difference spectra of cytochrome f in isolated thylakoid membranes (Melis et al., 1996). FIG. 5 shows that the amount of all three functional components declined with time under sulfur deprivation, with PSII (Q$_A$,) declining faster than P700 and Cytf.

It is evident that loss of PSII centers that are functional in charge separation (FIG. 5, Q$_A$/half-time of 40 h) is considerably slower than the loss of O$_2$ evolution activity in the cells (FIG. 1, P, half-time of 20 h). These results are consistent with the notion that sulfur deprivation first causes a conversion of PSII centers from the Q$_B$-reducing to a Q$_B$ nonreducing form, followed by a slower loss of PSII centers from the chloroplast thylakoids. This notion was supported by results of western blot analyses with antibodies specific for the various reaction center proteins of PSII and PSI (not shown). Thus, the response of the cells to sulfur deprivation suggests a strategy designed, first, to decrease the generation of O$_2$ thus avoiding severe oxidative damage under conditions of limited protein biosynthesis; and, second, to recycle existing proteins, releasing sulfur internally to be used in the biosynthesis of proteins indispensable for the survival of the organism.

Figure 6:
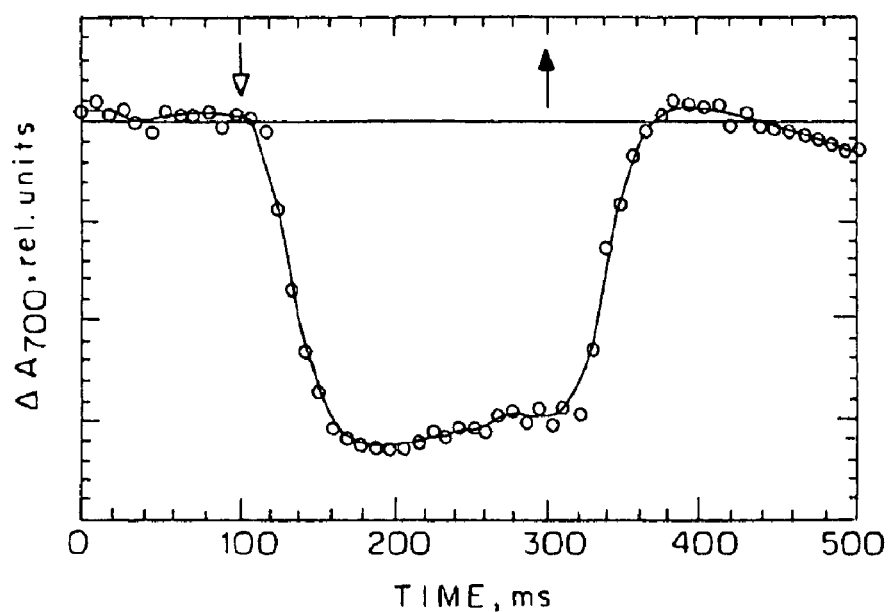
FIG. 6. In vivo light-induced absorbance change measurements of P700 ($\Delta A_{700}$) in *C. reinhardtii*, sulfur-deprived for 48 h. Cells were suspended in the presence of 20 $\mu$M DCMU. The time response of the apparatus was limited, through the use of electronic filters, to 15 ms. Saturating blue actinic excitation (CS 4-96 Corning glass filter, 250 $\mu$mol photons m$^{-2}$ s$^{-1}$) came ON at 100 ms (open arrow) and went OFF at 300 ms (filled arrow).

In addition to reduced levels of functional PSII, the photobiological production of H$_2$ requires the presence and operation of PSI. Only PSI is capable of generating reduced intermediates (e.g., reduced ferredoxin) with a sufficiently negative midpoint redox potential for the generation of molecular H$_2$. FIG. 5 (Cytf and P700) shows that significant amounts of Cyt f and P700 are retained in the thylakoid membrane throughout the 120 h sulfur-deprivation period. Besides transporting electrons from PSII-catalyzed water oxidation, cytochrome b$_6$-f and PSI may also be used for the transport of electrons from organic substrate, in a chlororespiration-type process to ferredoxin and the reversible hydrogenase. Photosystem-I activity during this H$_2$ production process, supported by electrons from organic substrate, was shown by in vivo measurements of the photooxidation and recovery kinetics of P700 in sulfur-deprived cells that were suspended in the presence of the PSII electron transport inhibitor DCMU. FIG. 6 shows such a kinetic trace in which actinic excitation (administered at 100 ms) caused a negative absorbance change at 700 nm (oxidation of P700 in the sample). When actinic excitation was turned off at 300 ms, P700 was reduced promptly in the dark with kinetics in the ms time range. The fast recovery of P700 in the dark suggests an abundance of electrons in the intersystem electron transport chain (plastoquinone, cytochrome $b_6f$ and plastocyanine). The presence, or absence, of DCMU had no effect on the observed light-induced oxidation or dark recovery kinetics (results not shown), consistent with the absence of electron donation by PSII, but see the explanation described below. This repetitive light-induced oxidation and dark-recovery pattern was kinetically identical in all samples examined throughout the 120 h sulfur-deprivation period, consistent with the active operation of an electron-transport pathway that involves some electron donation from organic substrate to the thylakoid membrane of C. reinhardtii, probably at the level of the plastoquinone pool.

However, when the residual PSII activity was completely inhibited by addition of DCMU to $H_2$-producing C. reinhardtii cultures, the rate of $H_2$ gas collection dropped to about 20% of its initial value. Total inhibition of $H_2$ gas collection was accomplished by addition of DBMIB, a chemical that affects the oxidation of the plastoquinone pool by the cytochrome b6/f complex, and thus inhibits electron transport from both PSII (water oxidation) and the chlororespiratory pathway (endogenous substrates) to the hydrogenase. These results are in clear contradiction with FIG. 6, and may be explained by differences in the time frame of the two experiments (seconds vs. hours). We, thus, conclude that most of the reductants for $H_2$ production are generated by residual water oxidation activity in sulfur-depleted C. reinhardtii cultures, but that an endogenous substrate may also contribute electrons for the process.

Figure 7:
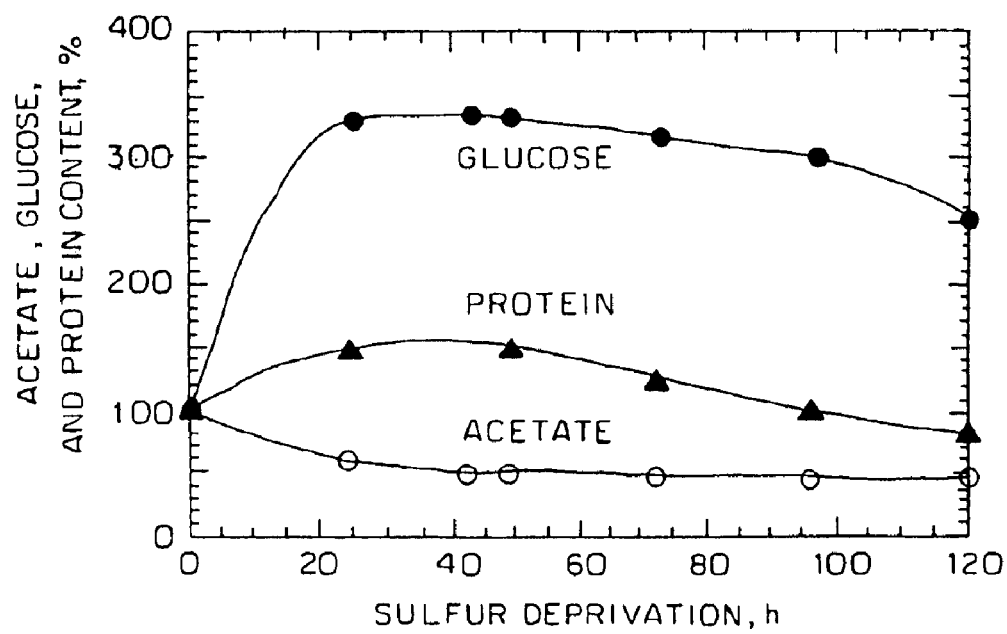
FIG. 7. Acetate, protein and starch (measured as total glucose) contents in *C. reinhardtii* as a function of time in the absence of sulfur. The absolute values at zero time, corresponding to culture densities of $6 \times 10^6$ cells/ml, were: acetate=15 $\mu$mol/ml, starch=16 nmol glucose/ml, and protein=150 $\mu$g/ml.

Various metabolites could be the source of extra electrons for this photobiological $H_2$ production process through the chlororespiratory pathway, including acetate, carbohydrate, lipid, protein and organic acids including the citric acid cycle and the glycolysis pathway. Acetate and starch are likely candidates for a chlororespiratory substrate in C. reinhardtii. FIG. 7 (Acetate) shows that the amount of acetate in the culture medium declined by about 50% during the 0–30 h period after sulfur deprivation. However, it remained stable at this level during the 30–120 h period and even started to increase slightly thereafter (data points beyond 120 h, not shown). These results suggest that acetate is consumed by respiration for as long as there is $O_2$, in the culture medium (0–30 h), but it does not contribute significantly as the source of electrons in the $H_2$-production process (30–120 h). Consistent with this interpretation are also measurements of the pH in the culture medium. The pH increased (from 7.5 to 8.2) during the 0–30 h period of aerobic incubation in the absence of sulfur, consistent with the uptake and utilization of acetate, and the concomitant release of hydroxide anion as a by-product of this reaction. Once anaerobiosis was established (t>30 h), however, this pH increase was gradually reversed (from 8.2 to 8.0), consistent with the notion of a light-dependent catabolic pathway that resulted in the elimination of residual photosynthetic oxygen, the formation of $CO_2$, and possibly the formation of some $H_2$ gas. The majority of the released $CO_2$ was trapped in the culture medium (FIG. 2), presumably as bicarbonate anion ($CO_2 + H_2O \rightarrow HCO_3^- \mathrm{---} + H^+$) due to the high pH value of the solution in the culture medium.

The amount of starch in the cells (equivalent to 16 nmol glucose per ml culture), increased transiently by about 330% in the first 25 h of sulfur deprivation, and subsequently declined slightly during the sulfur deprivation period (FIG. 7, Glucose). Starch catabolism cannot be the source of the organic substrate that feeds electrons into the reversible hydrogenase pathway since the absolute starch content of the culture (μmol quantities of glucose per L) is not sufficient to account for the mmol quantities of $H_2$ produced (see below). Quantitation of cellular protein in the sulfur-deprived cultures showed that the amount of protein (150 μg per ml culture) also increased transiently to about 150% of the initial in the 0–30 h period. Thereafter, and concomitant with the $H_2$ production activity, the level of protein in the culture declined to about 80% of the initial value at 120 h of sulfur deprivation (FIG. 7, Protein).

A quantitative summary of the $H_2$-production and substrate utilization data is given in TABLE 1.

TABLE 1

Substrate levels during $H_2$-production in *Chlamydomonas reinhardtii*

| Substrate | Amount Upon Sulfur Deprivation (0 h) | Amount Upon Culture Sealing | Amount After 80 h Of H2 Production | Change During H2-Production |
|---|---|---|---|---|
| $H_2$, ml | 0 | 0 | 140 | +140 |
| $H_2$, mmol | 0 | 0 | 4.67 | +4.67 |
| $CO_2$, mmol | 1.77 | 1.25 | 3.5 | +2.25 |
| Acetate, mmol | 15 | 7.6 | 8.2 | +0.6 (+8%) |
| Protein, mmol AA | 1.36 | 2.00 | 0.97 | −1.03 (−52%) |
| Starch, mmol glucose | $16 \times 10^{-3}$ | $52 \times 10^{-3}$ | $39 \times 10^{-3}$ | $-13 \times 10^{-3}$ |

Values correspond to 1 L cultures with densities of $6 \times 10^6$ cells/ml at the time of sulfur deprivation (t = 0 h). Hydrogen volume (ml) conversion to molarity (mmol) assumed 29.97 L/mol (at atmospheric pressure of 620 mm Hg at 1,600 m altitude) and 22.4 L/mol at (atmospheric pressure of 760 mm Hg at sea level). Protein weight conversion to mol assumed an average amino acid molecular weight of 110 g/mol.

Concomitant with the production of 4.67 mmol $H_2$, cells released 2.25 mmol $CO_2$ and a small amount of acetate into the medium. In addition, they consumed (presumably through catabolism) over 50% of the cellular protein, equivalent to about 1 mmol amino acid. Starch content declined by about 25%, equivalent to 13 μmol glucose, which is negligibly small to account for the production of 4.67 mmol $H_2$. A quantitative treatment of the results (i.e., amount of $H_2$ actually produced versus the protein consumed) suggests a $H_2$/amino acid ratio of 4.5:1. On the average, there are 10 gram atoms of H per amino acid for the 20 amino acid constituents of proteins. Although there is sufficient protein consumption to barely account for the reductant needed to supply the electrons for the light-dependent $H_2$-production process, the above inhibitor studies indicate that most of the electrons for $H_2$ production come from residual water-splitting capacity.

These results do not preclude the possibility that consumption of other cellular constituents and metabolites may also, directly or indirectly, contribute reductant to the reversible hydrogenase pathway, leading to $H_2$, production under these conditions. However, such a rigorous and detailed analysis is beyond the scope of the present work.

It is believed that *Chlamydomonas reinhardtii* cells produce molecular $H_2$ under these conditions because $H_2$ evolution is the only mechanism available to the algae for generating sufficient amounts of ATP required for the survival of the organism under sulfur-depleted anaerobic conditions.

The establishment of anaerobiosis by sulfur deprivation is an energy-dependent process that requires a carbon substrate for respiration. The main substrate for respiration in the initial 30 h of the sulfur-deprivation treatment is clearly acetate, as seen in FIG. 7. As the culture becomes anaerobic, acetate consumption stops and does not appear to play a role in the $H_2$-production process. Thus, the primary role of acetate is to help enhance cellular respiration and to establish anaerobiosis. In the absence of acetate, inhibition of PSII activity occurs much more slowly, and the cultures do not attain anaerobiosis during the 120 hour incubation period.

The $H_2$-production process is light-dependent and utilizes the reversible hydrogenase pathway under anaerobic conditions. The fermentative metabolism of *C. reinhardtii* in the light has been studied extensively. See, Gefeller, R. P. and Gibbs, M., *Plant Physiology*, 75: 212–218 (1984). The main products of starch photofermentation in the presence of DCMU (an inhibitor of PSII electron-transport and $O_2$ evolution, whose addition brings about results similar to those described here) were found to be $H_2$ and $CO_2$, in a ratio of 2.8:1. Formate and ethanol were present in much smaller amounts, and no acetate accumulation was detected. As seen in FIG. 7 and Table 1, little starch was present and little appeared to have been mobilized during the $H_2$-producing stage of the culture. Thus, starch was not the source of reductant for $H_2$ production. However, significant consumption of protein took place concomitantly with the $H_2$ production, suggesting that protein consumption is a key process in maintaining the cultures in an anaerobic state and thus active in $H_2$ production from water.

While the present invention has been illustrated and described with reference to particular structures and methods of fabrication, it will be apparent that other changes and modifications can be made therein with the scope of the present invention as defined by the appended claims.

We claim:

1. A reversible physiological process for temporal separation of oxygen evolution to avoid deactivation of hydrogenase in the presence of oxygen and sustain photosynthetic hydrogen production in cells of an algae microorganism, comprising:

(a) growing a culture of cells of algae microorganism photoheterotrophically in a Tris-acetate-phoshate medium under white fluorescence illumination conditions to accumulate an endogenous substrate;

(b) depleting a nutrient selected from the group consisting of sulfur, iron, and/or manganese from the medium in the presence of DCMU by suspending said culture of cells in the absence of said nutrient and sealing the culture of cells of algae microorganism from atmospheric oxygen until conditions become anaerobic;

(c) measuring the rate of cellular oxidative respiration in m mol $O_2$(mol Chl)$^{-1}$s$^{-1}$ of a sample of cells of said suspended algae microorganism from step (b) in the dark until it is constant or about 13 m mol $O_2$(mol chl)$^{-1}$s$^{-1}$;

(d) measuring the rate of $O_2$ evolution of a sample of the algae microorganism from step (c) under light of saturating intensity of yellow actinic excitation at about 1,300 $\mu$m photons m$^{-2}$s$^{-2}$;

(e) inducing reversible hydrogenase through photosynthesis by controlling the light saturated rate of oxygen production from the culture of cells of algae microorganism of step (b) so that it is equal to or less than the constant or 13 $\mu$mol $O_2$(mol Chl)-$^1$s$^{-1}$ rate of cellular oxidative respiration using saturating blue actinic excitation at 250 $\mu$mol photons m$^{-2}$s$^{-1}$ at 700 nm to generate an evolved gas that includes hydrogen.

2. The process of claim 1 wherein said hydrogen is generated from water and the accumulated endogenous substrate.

3. The process of claim 1 wherein depleting is to a concentration of 0.5 millimolar or less.

4. The process of claim 1 further comprising repeating steps (a) through (e) for a plurality of cycles.

5. The process of claim 2 wherein the microorganism is selected from the group consisting of green, red, brown, and blue-green algae.

6. The process of claim 2 further comprising repeating steps (a) through (e) for a plurality of cycles.

7. The process of claim 2 wherein the substrate is selected from the group consisting of acetate, carbohydrate, lipid and protein.

8. The process of claim 5 wherein the algae is *Chlamydomonas reinhardtii*.

* * * * *